(12) United States Patent
Bencsits

(10) Patent No.: US 8,481,063 B2
(45) Date of Patent: Jul. 9, 2013

(54) INSECT REPELLENT

(75) Inventor: Franz Bencsits, Klosterneuburg (AT)

(73) Assignee: Fulltec AG, Zug (CH)

( * ) Notice: Subject to any disclaimer, the term of this patent is extended or adjusted under 35 U.S.C. 154(b) by 1979 days.

(21) Appl. No.: 10/485,678

(22) PCT Filed: Jul. 23, 2002

(86) PCT No.: PCT/EP02/08216
§ 371 (c)(1),
(2), (4) Date: Jun. 18, 2004

(87) PCT Pub. No.: WO03/011805
PCT Pub. Date: Feb. 13, 2003

(65) Prior Publication Data
US 2004/0265349 A1    Dec. 30, 2004

(30) Foreign Application Priority Data
Jul. 30, 2001   (DE) .................................. 101 37 085

(51) Int. Cl.
*A01N 25/32* (2006.01)
*A01N 35/021* (2006.01)

(52) U.S. Cl.
USPC ........... 424/406; 424/405; 424/407; 424/409; 424/DIG. 10; 514/558; 514/703; 514/919

(58) Field of Classification Search
None
See application file for complete search history.

(56) References Cited

U.S. PATENT DOCUMENTS

| | | | | |
|---|---|---|---|---|
| 3,869,517 A | * | 3/1975 | Gradeff et al. | 568/458 |
| 4,605,783 A | * | 8/1986 | Zinnen | 568/492 |
| 4,608,263 A | * | 8/1986 | Bergin et al. | 426/303 |
| 4,707,496 A | * | 11/1987 | Simmons | 514/531 |
| 5,130,136 A | * | 7/1992 | Shono et al. | 424/405 |
| 5,182,105 A | * | 1/1993 | Takata et al. | 424/78.02 |
| 5,589,181 A | * | 12/1996 | Bencsits | 424/405 |
| 5,626,854 A | * | 5/1997 | Ichii et al. | 424/401 |
| 5,959,161 A | | 9/1999 | Kenmochi et al. | 568/833 |
| 6,306,415 B1 | * | 10/2001 | Reifenrath | 424/406 |
| 6,455,086 B1 | * | 9/2002 | Trinh et al. | 426/321 |
| 7,109,240 B2 | * | 9/2006 | Bessette et al. | 514/546 |

FOREIGN PATENT DOCUMENTS

| | | |
|---|---|---|
| BR | 200001980 A | 1/2002 |
| EP | 0 216 416 A2 | 4/1987 |
| EP | 0 495 684 A1 | 7/1992 |
| JP | 05294828 A | 11/1993 |
| SU | 1544435 | 2/1990 |
| WO | WO 94/04029 | 3/1994 |
| WO | WO 96/00056 | 1/1996 |
| WO | WO 97/49380 | 12/1997 |
| WO | WO 00/49865 A | 8/2000 |
| WO | WO 02/55648 | 7/2002 |

OTHER PUBLICATIONS

Search Report for PCT/EP02/08216.
IPER for PCT/EP02/08216.
Inagaki et al., "Enantioselective Esterification of Racemic Terpene Alcohols with Fatty Acids by *Pseudomonas sp.* NOF-5 Strain," Agric. Biol. Chem., 51 (5) pp. 1345-1348 (1987).
Ishino et al., "Synthesis of Hydroxycitronellal. Hydration and Subsequent Hydrolysis of Imines, Enamines, or Oxazolidines Prepared from Citronellal and Amines," J. Org. Chem., vol. 39, No. 1 (1974).

* cited by examiner

*Primary Examiner* — Neil Levy
(74) *Attorney, Agent, or Firm* — Kilyk & Bowersox, P.L.L.C.

(57) ABSTRACT

The present invention relates to a hydrated compound of an unsaturated monoterpenoid as well as its use as insect repellent.

5 Claims, No Drawings

INSECT REPELLENT

This application in a National Stage entry of International Application No. PCT/EP02/08216, and claims the benefit of earlier filed International Application No. PCT/EP02/08216 filed Jul. 23, 2002.

The present invention relates to an insect repellent (Repellent) against flying, stinging, biting and sucking insects as well as pests of the genus *Acarina* (mites and ticks).

Repellents are chemical substances which have a repulsive activity with respect to insects and *Acarina*. Practical importance has the use of these repellents in the section of human and veterinary hygiene in order to protect human and animals from the activity of blood sucking, stinging and biting pests which are not only bothersome but also possess the potential to transmit diseases (malaria, FSME, Lyme-Borreliose and others). Repellents which are to be used and applied directly onto the skin must be compatible with skin, non-toxic, lightfast and sweatfast and also must be acceptable from a cosmetic view, i.e. not problematic to the skin (drying, generation of wrinkles) as well as unproblematic from the pharmacological view (irritation, penetration into deeper layers of the skin and penetration into the blood cycle or the lymph cycle). Furthermore, the protection of the treated areas of the skin or the protection of human and animals by using treated products should be maintained as long as possible and the activity of the repellent should be as broad as possible, i.e. the repellent should be active against a lot of different pests.

In the past and as well as, to a lesser extent, at present, etherial oils such as citronella oil and lemon grass oil as well as clove oil, lavender oil, eucalyptus oil, as well as camphor are used as repellents. These products show the following drawbacks:
  they may contain problematic components, such as for example eugenol in clove oil which has, in experiments, shown mutagenic, carcinogenic and skin irritating activity or cineol in the oil obtained from *eucalyptus globulus*, which immediately is able to give rise to tingling exanthems.
  they may only show a short term activity, since the etheric oils are evaporated from the skin due to the body temperature, so that reapplications become necessary in order to obtain the desired protection.
  insufficient lightfastness may give rise to phytosensitation as well as change of the product before application.

In the recent past, the above-discussed repellents have been replaced by synthetic repellents. Synthetic repellents known in the prior art are for example phthalic acid dimethylesters, 1,2-ethylhexane-1.3-diol, 3,4-dihydro-2,2-dimethyl-4-oxo-2H-pyrane-6-carboxylic acid-n-butylester, succinic acid dipropylester, N,N-diethyl-3-methylbenzamide (DEET, also named N,N-diethyl-m-toluamide) and pyridine-2,5-dicarboxylic acid-di-n-propylester (Ullmanns Encyclopedia of Technical Chemistry, 4th edition, volume 13, page 237 and onwards, 1977). In the recent past, mainly hydroxyethyl-butyl-piperidin-carboxylate (1-piperidincarboxylic acid-2-(2-hydroxyethyl)-1-methylpropylester) is used. However, these synthetic repellents often do not possess the required sweatfastness, irritate mucous membranes and are furthermore also able to penetrate through the upper most layer of the skin so that accumulation in the body may occur, in which connection it must be noted that the resulting side effects have not yet been established fully although the general approach is that negative results are to be expected.

Accordingly, the object of the present invention is to provide a compound which is able to be used as active insect repellent directly on the skin and/or on clothing and/or on other materials or products which are in contact or are used in the vicinity of the individual which has to be protected (bed linen, table cloth and other materials). These compounds should be based on natural products or products identical to natural products having a very low toxicological risk, which furthermore should provide a high activity over a prolonged time.

In accordance with the present invention, this object is solved with a hydrated compound of an unsaturated monoterpenoid. Monoterpenoids are dimeric products of isoprene (2-methyl-1,3-butadien, $C_5H_8$) which possess a $C_{10}$ skeleton. Monoterpenoids may be acyclic, monocyclic and bicyclic.

Preferred monoterpenoids are citronellal or isomers thereof and p-menthenol and isomers thereof. As p-menthenol preferably isopulegol or isomers thereof are used. Further examples of p-menthenols are for example shown in Rompp, Lexicon Naturstoffe, 1997, p. 393.

(±)—CITRONELLAL [(±)-3,7-Dimethyl-6-octanal] has the following formula:

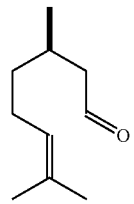

(±)—ISOPULEGOL [2-Isopropenyl-5-methyl-cyclohexanol] has the following formula:

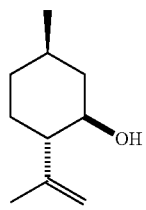

The unsaturated monoterpenoids may be obtained in the form of an etherial oil using steam distillation and the leaves of *eucalyptus citriodora* hook (natural; according to INCI: *eucalyptus citriodora*, CAS: 800048-4, EINECS: 283406-20, main components: 70 to 90% citronellal and isopulegol).

It is also possible to use synthetic citronellal, obtained starting from geraniol, nerol, citronellol and/or citral. Isopulegol may be obtained by isomerization of citronellal using known methods.

Furthermore, the above object is solved with a composition, comprising the compound in accordance with the present invention and a $C_6$-$C_{13}$ carboxylic acid. The carboxylic acid to be used in accordance with the present invention may be a natural one or a synthetic one and also may be a mixture thereof.

The carboxylic acids obtained from natural resources may be of vegetable or animal origin. Preferably they are obtained from fatty oils or etherial oils such as coconut oil, palm oil, calamus oil, geranium oil, thyme oil, iris oil, butter or tallum. The processes necessary for obtaining carboxylic acids from these natural products are known to the skilled person and they comprise fatty splitting by saponification or hydrolysis using an autoclave in accordance with the Twitchell process or pressure cleavage using steam. Starting materials for synthetic products may be alcohols and/or aldehydes as well as aliphatic or acyclic hydrocarbons, which may be converted into fatty acids using known processes such as Oxo-synthesis, Reppe-synthesis, Koch-Haaf synthesis, carbonylation reactions or saponification of nitriles. Preferred carboxylic acids, alone or in mixture, are caproic acid, caprylic acid, nonanoic acid, capric acid, undecylenic acids (in particular 10-undecylenic acid), undecanoic acid, lauric acid and tridecanoic acid. Preferred as carboxylic acid is lauric acid (carboxylic acid $C_{12}$, dodecanoic acid) $CH_3(CH_2)_{10}COOH$.

The compound in accordance with the present invention or the composition in accordance with the present invention may be used as insect repellent.

Furthermore, the compound in accordance with the present invention or the composition in accordance with the present invention may be used in the form of the following products: emulsion, dispersion, lotion, cream, gel or solution.

In order to prepare those products, the processes known in the art may be used. Furthermore, the known components and additives of such products may be used, comprising solvents, dissolution accelerators, emulgators, dissolution enhancers, surface active agents, anti-foaming agents, salts, buffers, gel-forming agents, thickeners, film-forming agents, binders, lubricants, anti-sticking agents, flow regulating agents, moisturizers and drying agents, fillers and auxiliary additives, such as antioxidants, preservatives, odor correcting agents and colorants.

The term "emulsion" defines all dispersed systems comprising two or more liquids which are not mixable, wherein the components of the emulsion may also be present as solids at room temperature. These emulsions may be macro emulsions and micro emulsions. Typically, water in oil emulsions or oil in water emulsions are used. In order to reduce the necessary interface work (energy necessary for obtaining an emulsion) emulsifiers may be used. Emulsifiers typically are surface active compounds, which normally comprise hydrophilic end groups.

Typical examples thereof are as follows:
a) anionic emulsifiers, i.e. emulsifiers comprising carboxylate, sulfonate, sulfate, phosphate, polyphosphate, lactate, citrate, tartrate, glucose or polyglucose end groups;
b) cationic emulsifiers, i.e. emulsifiers having an amine salt end group or quarternary ammonium end groups;
c) amphoteric and zwitterionic emulsifiers, i.e. emulsifiers having zwitterionic end groups or a betain end group;
d) non-ionic emulsifiers, i.e. emulsifiers having alcohol, polyether, glycerine, sorbite, pentaerythrite, saccharose, acetic acid and/or lactic acid groups in the end group.

All emulsifiers furthermore comprise furthermore lipophilic end groups, such as alkyl or alkenyl groups which may be straight, branched or cyclic as well as aryl groups or alkyl aryl groups. Furthermore, hydrophilic side chains, such as hydroxyl, ester, sulfamide, amide, amine, polyamide, ether, polyether, glycerine, sorbite, pentaerytherite, or saccharose groups may be comprised.

The term "gels" comprises dimensionally stable systems which are easily deformed and which are liquid rich, where in the system comprises at least two components. Typically, these two components are one liquid and one solid, colloidal dispersed compound, such as gelatine, silicic acid, montmorillonite, bentonit, polysaccharide, polyacrylate and pektine.

Hydratation preferably occurs directly during the preparation of the products in the form of aqueous products, wherein as catalyst organic acids, such as citric acid, benzoic acid, lactic acid, sorbic acid, maleic acid, tartaric acid, maltonic acid, fumaric acid and succinic acid may be used. Principally, as catalysts, all hydroxy carboxylic acids and dicarboxylic acids are usable. However, due to toxicologic and dermatologic considerations, citric acid, benzoic acid, lactic acid, sorbic acid, malleic acid and tartaric acid are preferred, in particular in view of the fact that they are not consumed due to their function as catalysts or due to any other chemical reaction but may be maintained in the product as natural and compatible pH stabilizers and preservatives.

Hydratation is the process wherein due to a chemical reaction, H and OH from water are bound covalently to two neighboring atoms. This reaction must not be mistakenly be taken as hydration (solvation using water as solvent).

The following structure shows as one example of isopulegol-hydrate, the most active compound of the hydrates and hydroxyls which are isomeric to citronellal.

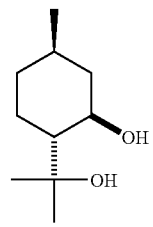

The preparation may occur as follows: water is heated to 38 to 42° C., preferably 40° C., and the acid(s) to be used as catalysts are dissolved therein. The solution is maintained at the temperature and the unsaturated monoterpenoid is added. Using an appropriate device, this mixture is stirred for approximately 6 hours, after which the hydratation has occurred. The final product as active ingredient, i.e. the hydrated monoterpenoid can be detected using MS (mass spectroscopy).

Furthermore, the hydratation may be carried out using an appropriate device, which for example may be present in a lot of industrial chemistry plants. Furthermore, usual catalysts, such as metal compounds may be used and the obtained hydrates can then be used directly as raw material for repellent products.

Examples of such metallic catalysts are: tungsten (VI) oxychloride, mercury (II) acetate, magnesium methyl carbonate, magnesium trifluoromethansulfonate. Tungsten (VI) oxychloride is the preferred catalyst.

Furthermore, other catalysts, selected in accordance with the reactor to be used, may be employed.

A further advantage of the compositions in accordance with the present invention is that stable alcohol free compositions are possible which require only a very low amounts of emulsifier, which are furthermore due to their properties (lack of skin irritation and skin drying properties, which are latent problems associated with alcohol application on skin) good for application on problematic skin areas as well as on small children.

The preparation occurs using the general principle for the preparation of an emulsion. Water is warmed to approximately 65° C., the acids are dissolved therein and $C_6$-$C_{13}$ carboxylic acid is introduced into this aqueous solution, wherein the carboxylic acid has been melted separately at about 55° C. In addition, a non-ionic emulgator, for example PEG-40 hydrogenated castor oil is introduced, emulgation occurs using a suitable device, followed by cooling to 40° C. At this temperature, citronellal and/or isopulegol is introduced and stirring is continued until hydratation has occurred, using the acid catalyst. The only requirement for the complete hydratation is the presence of enough amounts of water. The minimum ratio is one part water respective to ten parts unsaturated monoterpenoid.

Furthermore, compositions using a synthetic hydrated monoterpenoid may be used, produced in accordance with the above disclosure.

In the following the present invention is illustrated further by means of the given examples.

EXAMPLES

The following Examples 1 to 12 show compositions which have been tested as insect repellent. Examples 1 and 2 do not contain hydrated monoterpenoids. Examples 3 and 4 contain monoterpenoids which have been hydrated during the preparation of the product and Examples 5 and 6 use monoterpenoids which have been hydrated previously. Examples 7 and 8 show compositions in accordance with the present invention wherein hydratation again has occurred during the preparation of the products.

| Example 1: | Example 2: |
|---|---|
| 50.00 wt. % *Eucalyptus citriodora* oil | 25.00 wt. % Citronellal |
| 50.00 wt. % Isopropyl alcohol | 25.00 wt. % Isopulegol |
| | 50.00 wt. % Isopropylakohol |

| Example 3: | Example 4: |
|---|---|
| 25.00 wt. % Water | 25.00 wt. % Water |
| 2.00 wt. % Benzoic acid | 2.00 wt. % Benzoic acid |
| 0.50 wt. % Citric acid | 0.50 wt. % Citric acid |
| 25.00 wt. % *Eucalyptus citriodora* oil | 10.00 wt. % Citronellal |
| 47.50 wt. % Isopropyl alcohol | 10.00 wt. % Isopulegol |
| | 52.50 wt. % Isopropyl alcohol |

| Example 5: | Example 6: |
|---|---|
| 30.00 wt. % Water | 30.00 wt. % Water |
| 10.00 wt. % Citronellal-hydrat | 10.00 wt. % Isopulegol-hydrat |
| 60.00 wt. % Isopropyl alcohol | 60.00 wt. % Isopropyl alcohol |

| Example 7: | Example 8: |
|---|---|
| 66.50 wt. % Water | 66.50 wt. % Water |
| 2.00 wt. % Benzoic acid | 2.00 wt. % Benzoic acid |
| 0.50 wt. % Citric acid | 0.50 wt. % Citric acid |
| 20.00 wt. % Citronellal | 20.00 wt. % Isopulegol |
| 1.00 wt. % PEG-40 Castor oil hydrogenat. | 1.00 wt. % PEG-40 Castor oil hydrogenat. |
| 10.00 wt. % Lauric acid | 10.00 wt. % Lauric acid |

| Example 9: | Example 10: |
|---|---|
| 72.00 wt. % Water | 62.00 wt. % Water |
| 2.00 wt. % Citric acid | 2.00 wt. % Citric acid |
| 20.00 wt. % Citronellal | 20.00 wt. % Isopulegol |
| 1.00 wt. % PEG-40 Castor oil hydrog. | 1.00 wt. % PEG-40 Castor oil hydrog. |
| 5.00 wt. % Lauric acid | 15.00 wt. % Lauric acid |

| Example 11: | Example 12: |
|---|---|
| 66.50 wt. % Water | 66.50 wt. % Water |
| 2.00 wt. % Benzoic acid | 2.00 wt. % Benzoic acid |
| 0.50 wt. % Citric acid | 0.50 wt. % Citric acid |
| 20.00 wt. % Citronellal | 20.00 wt. % Citronellal |
| 1.00 wt. % PEG-40 Castor oil hydrogenat. | 1.00 wt. % PEG-40 Castor oil hydrogenat. |
| 10.00 wt. % Lauric acid | 10.00 wt. % Lauric acid |

In respect of Examples 9 and 12, the following reference samples were prepared:

| | REF 2: | REF 3: | REF 4: | REF 5: |
|---|---|---|---|---|
| Water | 91.50 | 81.50 | 86.50 | 86.50 |
| Benzoic acid | 2.00 | 2.00 | 2.00 | 2.00 |
| Citric acid | 0.50 | 0.50 | 0.50 | 0.50 |
| PEG-40 hyd. Castrol Oil | 1.00 | 1.00 | 1.00 | 1.00 |
| Lauric acid | 5.00 | 15.00 | — | — |
| Capric acid | — | — | 10.00 | — |
| Caprylic acid | — | — | — | 10.00 |

The unsaturated monoterpenoids are obtained in the form of an etherial oil by using steam distillation of the leaves of *eucalyptus citriodora* hook (natural, INCI: *eucalyptus citriodora*, CAS: 8000484, EINECS: 283406-2, main components: 70 to 90% citronellal and isopulegol).

The tests results disclosed below show that the increase of activity, using citronellal or isopulegol or mixtures of both isomers (Example 2) compared with etherial oil from *eucalyptus citriodora* (Example 1) is not yet significant. Surprisingly, a significant increase of the duration and the intensity of the repellent activity, for all tested pests, occurs if hydrated *eucalyptus citriodora* oil or hydrated citronellal and/or hydrated isopulegol are used (Examples 3 to 6). A further surprising and very significant increase of activity can be obtained if a carboxylic acid as defined above, in particular lauric acid ($C_{12}H_{24}O_2$ (Examples 7 and 8)) is added.

1. Test Series of Repellent Compositions with Respect to Mosquitoes and Humans

The insect repellents of Examples 1 to 8 were tested using two test persons. As reference, a product obtained in the market (KIK AKTIV® comprising 30% DEET (N,N-diethyl-m-toluamide)) was used.

The right forearm of every test person was treated on an area of 250 cm$^2$ with the desired product (Examples 1 to 8). An amount of 2 ml of each composition was distributed evenly on the area. The treated area of the forearm was closed with respect to the hand and with the remaining arm using an adhesive and short plastic hoses. The untreated hand was covered using a thick glove so that a control of the biting activity of the mosquitoes could be carried out, since the mosquitoes tried to sit down on the glove and attempt to bite through the glove into the skin below. The left forearm was, in the same manner, treated with the reference product (REF). As mosquitoes in each test (example applied on the right forearm versus reference applied on the left forearm) 300 to 400 female yellow fever mosquitoes were used in a test volume of 40×40×40 cm$^3$. This is a population which usually does not occur in nature so that a good differentiation between the activity of the compositions can be obtained. REF2 to REF 5 were tested in a similar manner.

For the test, the hand and the forearm, after a delay of 1 hour after application of the composition, first the left arm comprising REF and then the right arm comprising EX were inserted every hour for 10 minutes into the test volume and during this time the numbers of mosquitoes were noted with respect to the following four incidents:

(a) number of mosquitoes trying to bite through the gloves (positive control)
(b) number of mosquitoes which fly towards the treated area but turn away in a distance of below 3 cm (repulsive activity)
(c) number of mosquitoes sitting down on the treated area for more than 2 seconds but which do not bite
(d) number of mosquitoes which sit down on the treated area and which bite and suck blood Each of the two test persons tested each of the eight examples. However, each test person conducted only one test per day in order to reduce the danger of product accumulation and possible cross reactions of products due to insufficient cleaning of the skin.

| | | Results Test Person 1 | | | | | | | |
|---|---|---|---|---|---|---|---|---|---|
| Time after application | Duration of exposition | Number of mosquitoes sitting down on gloves (a) | | Number of mosquitoes flying towards treated area (b) | | Number of mosquitoes sitting down (c) | | Number of bites (d) | |
| | | EX1 | REF | EX1 | REF | EX1 | REF | EX1 | REF |
| 1 h | 1 min. | 120 | 130 | 32 | 0 | 32 | 0 | 32 | 0 |
| | | EX2 | REF | EX2 | REF | EX2 | REF | EX2 | REF |
| 1 h | 10 mins. | 150 | 120 | 48 | 0 | 18 | 0 | 0 | 0 |
| 2 h | 1 min. | 100 | 100 | 40 | 0 | 36 | 0 | 32 | 0 |
| | | EX3 | REF | EX3 | REF | EX3 | REF | EX3 | REF |
| 1 h | 10 mins. | 140 | 120 | 0 | 0 | 0 | 0 | 0 | 0 |
| 2 h | 10 mins. | 100 | 120 | 0 | 0 | 0 | 0 | 0 | 0 |
| 3 h | 10 mins. | 100 | 100 | 3 | 0 | 0 | 0 | 0 | 0 |
| 4 h | 10 mins. | 120 | 100 | 8 | 0 | 0 | 0 | 0 | 0 |
| 5 h | 10 mins. | 150 | 120 | 23 | 6 | 2 | 0 | 0 | 0 |
| 6 h | 10 mins. | 150 | 130 | 45 | 12 | 8 | 2 | 3 | 0 |
| | | EX4 | REF | EX4 | REF | EX4 | REF | EX4 | REF |
| 1 h | 10 mins. | 100 | 130 | 0 | 0 | 0 | 0 | 0 | 0 |
| 2 h | 10 mins. | 110 | 110 | 0 | 0 | 0 | 0 | 0 | 0 |
| 3 h | 10 mins. | 110 | 120 | 0 | 0 | 0 | 0 | 0 | 0 |
| 4 h | 10 mins. | 130 | 130 | 0 | 0 | 0 | 0 | 0 | 0 |
| 5 h | 10 mins. | 100 | 150 | 4 | 12 | 0 | 2 | 0 | 0 |
| 6 h | 10 mins. | 100 | 130 | 9 | 16 | 0 | 6 | 0 | 0 |
| 7 h | 10 mins. | 150 | 140 | 21 | 33 | 4 | 11 | 0 | 1 |
| 8 h | 10 mins. | 120 | 100 | 34 | 38 | 17 | 17 | 2 | 6 |
| | | EX5 | REF | EX5 | REF | EX5 | REF | EX5 | REF |
| 1 h | 10 mins. | 100 | 120 | 0 | 0 | 0 | 0 | 0 | 0 |
| 2 h | 10 mins. | 130 | 100 | 3 | 0 | 0 | 0 | 0 | 0 |
| 3 h | 10 mins. | 110 | 120 | 8 | 0 | 1 | 0 | 0 | 0 |
| 4 h | 10 mins. | 100 | 140 | 16 | 0 | 6 | 0 | 2 | 0 |
| 5 h | 10 mins. | 150 | 160 | 27 | 9 | 11 | 0 | 5 | 0 |
| | | EX6 | REF | EX6 | REF | EX6 | REF | EX6 | REF |
| 1 h | 10 mins. | 120 | 100 | 0 | 0 | 0 | 0 | 0 | 0 |
| 2 h | 10 mins. | 120 | 120 | 0 | 0 | 0 | 0 | 0 | 0 |
| 3 h | 10 mins. | 150 | 100 | 0 | 0 | 0 | 0 | 0 | 0 |
| 4 h | 10 mins. | 120 | 120 | 0 | 0 | 0 | 0 | 0 | 0 |
| 5 h | 10 mins. | 110 | 120 | 0 | 5 | 0 | 0 | 0 | 0 |
| 6 h | 10 mins. | 150 | 130 | 4 | 12 | 2 | 5 | 0 | 0 |
| 7 h | 10 mins. | 130 | 100 | 35 | 20 | 21 | 12 | 14 | 2 |

| 1 | 2 | a | b | c | d | a | b | c | d | a | b | c | d | a | b | c | D |
|---|---|---|---|---|---|---|---|---|---|---|---|---|---|---|---|---|---|
| Product | | EX9 | | | | EX10 | | | | EX11 | | | | EX12 | | | |
| 1 | 10 | 120 | 0 | 0 | 0 | 120 | 0 | 0 | 0 | 110 | 0 | 0 | 0 | 100 | 0 | 0 | 0 |
| 2 | 10 | 110 | 0 | 0 | 0 | 130 | 0 | 0 | 0 | 110 | 0 | 0 | 0 | 90 | 0 | 0 | 0 |
| 3 | 10 | 110 | 0 | 0 | 0 | 120 | 0 | 0 | 0 | 120 | 0 | 0 | 0 | 90 | 0 | 0 | 0 |
| 4 | 10 | 120 | 0 | 0 | 0 | 120 | 0 | 0 | 0 | 110 | 0 | 0 | 0 | 100 | 0 | 0 | 0 |
| 5 | 10 | 120 | 0 | 0 | 0 | 130 | 0 | 0 | 0 | 130 | 0 | 0 | 0 | 110 | 0 | 0 | 0 |
| 6 | 10 | 110 | 2 | 0 | 0 | 120 | 0 | 0 | 0 | 120 | 0 | 0 | 0 | 120 | 0 | 0 | 0 |
| 7 | 10 | 110 | 14 | 4 | 0 | 120 | 0 | 0 | 0 | 120 | 5 | 0 | 0 | 120 | 7 | 0 | 0 |
| 8 | 10 | 50 | 13 | 5 | 3(4)* | 130 | 0 | 0 | 0 | 90 | 10 | 0 | 0 | 100 | 15 | 3 | 0 |
| 9 | | | | | | 120 | 0 | 0 | 0 | 60 | 23 | 8 | 2(8)* | 90 | 5 | 3 | 3(2)* |
| 10 | | | | | | 90 | 5 | 0 | 0 | | | | | | | | |
| 11 | | | | | | 90 | 15 | 2 | 0 | | | | | | | | |
| 12 | | | | | | 70 | 14 | 4 | 1(9)* | | | | | | | | |

-continued

| | | | | | Results Test Person 1 | | | | | | | | | | | |
|---|---|---|---|---|---|---|---|---|---|---|---|---|---|---|---|---|
| 1 | 2 | a | b | c | d | a | b | c | d | a | b | c | d | a | b | C |
| Product | | | REF 2 | | | | REF 3 | | | | REF 4 | | | | REF 5 | |
| 1 | 10 | 100 | 8 | 2 | 0 | 110 | 0 | 0 | 0 | 130 | 0 | 0 | 0 | 130 | 3 | 0 |
| 2 | 10 | 60 | 30 | 18 | 4(1)* | 130 | 14 | 3 | 0 | 60 | 28 | 12 | 2(5)* | 50 | 10 | 2(6)* |
| 3 | 10 | | | | | 80 | 26 | 12 | 2(2)* | | | | | | | |

Legend:
1 = time after application of the product (hours)
2 = exposition duration per hour (10 minutes test) if bites occurred some tests were stopped and the respective reduced exposition time is given
a = number of mosquitoes sitting down on the glove
b = number of mosquitoes approaching the treated area but which turn away again without sitting down and which fly away again after sitting down for less than 2 seconds
c = number of mosquitoes sitting on the treated area for more than 2 seconds which, however, did not bite (together with the number of mosquitoes b above, this value represents the nuisance value)
d = number of mosquitoes sitting down and biting prior to the termination of the test
*= stop of the test due to the high number of bites The results obtained with EX1 and EX2 show that non-hydrated citronellal and non-hydrated isopulegol, occurring naturally in *eucalyptus citriodora* oil as well as obtained pure by synthesis, show only a limited repellence. The hydrated products EX3 and EX4, which have been hydrated during the preparation, as well as EX5 and EX6, in which citronellal and isopulegol have been hydrated synthetically beforehand, show a better repellence, wherein it further can be seen that the main active component is isopulegol-hydrate, since EX6 has a better activity compared with EX3, EX4 and EX5. However, even the activity of those products (EX3, EX4 and EX5 as well as EX6, EX7 and EX8) is high enough so that the approval of Tropical Institutes may be obtained. The requirements of these Tropical Institutes require that a product must protect a test person for 4 hours with respect to mosquito bites and that not more than 10% of the total number of mosquitoes sit down on the treated area without biting.

The tests using EX7 and EX8 were carried out using a new reference, since the activity of KIK ACTIV® is already known. Furthermore, it was intended to show that the lauric acid, employed as synergist, does only show a limited repellence if used alone. Accordingly, reference product REF 1 having the following composition was used:

76.5 wt. % water
2.0 wt. % benzoic acid
0.5 wt. % citric acid
1.0 wt. % PEG-40 hydrogenated castor oil
10.0 wt. % lauric acid

| | | EX7 | REF1 | EX7 | REF1 | EX7 | REF1 | EX7 | REF1 |
|---|---|---|---|---|---|---|---|---|---|
| 1 h | 10 min. | 150 | 130 | 0 | 16 | 0 | 4 | 0 | 0 |
| 2 h | 10 min. | 120 | 100 | 0 | *23 | 0 | *23 | 0 | *12 |
| 3 h | 10 min. | 140 | | 0 | | 0 | | 0 | |
| 4 h | 10 min. | 150 | | 0 | | 0 | | 0 | |
| 5 h | 10 min. | 130 | | 0 | | 0 | | 0 | |
| 6 h | 10 min. | 100 | | 0 | | 0 | | 0 | |
| 7 h | 10 min. | 120 | | 8 | | 0 | | 0 | |
| 8 h | 10 min. | 130 | | 15 | | 4 | | 0 | |
| 9 h | 10 min. | 100 | | 24 | | 10 | | 2 | |

*= Stopping of test after 2 minutes due to high number of bites

| | | EX8 | REF1 | EX8 | REF1 | EX8 | REF1 | EX8 | REF1 |
|---|---|---|---|---|---|---|---|---|---|
| 1 h | 10 min. | 130 | 120 | 0 | 14 | 0 | 6 | 0 | 0 |
| 2 h | 10 min. | 120 | 150 | 0 | *33 | 0 | *18 | 0 | *15 |
| 3 h | 10 min. | 140 | | 0 | | 0 | | 0 | |
| 4 h | 10 min. | 130 | | 0 | | 0 | | 0 | |
| 5 h | 10 min. | 120 | | 0 | | 0 | | 0 | |
| 6 h | 10 min. | 110 | | 0 | | 0 | | 0 | |
| 7 h | 10 min. | 120 | | 0 | | 0 | | 0 | |
| 8 h | 10 min. | 100 | | 0 | | 0 | | 0 | |
| 9 h | 10 min. | 100 | | 5 | | 0 | | 0 | |
| 10 h | 10 min. | 100 | | 12 | | 0 | | 0 | |

In particular, the results obtained with EX8 show the surprisingly improved repellence and prolongation of the duration of the activity obtained due to the use of the synergist. However, even the results of EX7 show this tendency when compared with the results of EX4.

2. Test Series of Repellent Compositions with Respect to Ticks Using Dogs

In order to evaluate the repellent activity concerning ticks, as typical representative of *Acarina*, which are the most dangerous species for human and animals and which are also widely distributed, a five-day test was carried out.

Six dogs of various origin and sex were employed (all from an animal shelter), which, however, had comparable weight. One test person walked with three dogs 4 hours per day through an area for which it had been established that it contained ticks (forest at the border of the new city of Vienna). Dogs marked V1 and V2 were treated with EX4 by applying 10 ml of the composition. Dogs designated V3 and V4 were treated in a similar manner with EX8 and the dog designated REF was treated with KIK ACTIV® and dog K (control) did not receive any treatment. The two persons walking with the dogs were treated on the whole body with 10 ml EX8 since the danger of the transmittal of borreliose by means of bites of ticks should be prevented, although the test person had been treated against FSME. At the same time this treatment should confirm the activity of this product over 4 hours against ticks, an activity which already had been established in the laboratory using the skin of guinea pig over 8 hours. As further measured in order to reduce the risk, shoes, socks, long trousers and the shirt of the test persons, which were tightened against the arms and legs, were treated daily with 5 ml EX8. After each daily 4-hour walk, the dogs as well as the human were evaluated with respect of the presence of ticks. If present, the ticks were placed into test glasses and observed for 72 hours.

Results
1. Human 1, Dog K and Dogs V1 and V1

On the skin of the Human 1 over five days, no ticks were found. Of the clothing, a total of four ticks were taken which, however, had not proceeded towards the skin of the human, in contrast to the Dog K. The ticks taken from Human 1 already immediately after removal from the clothing were evaluated as immobile. Those ticks did not show any revitalization over 72 hours, proving the mortal activity of EX8 towards ticks, which had been shown in the laboratory. From Dog K, during those five days, a total of 43 ticks were collected. All ticks did survive the 72-hour observation period, showing that the area was inhabitated with living ticks. Dogs V1 and V2 did not show any single tick.

2. Human 2, Dog REF and Dogs V3 and V4

The clothing of Human 2 did not show any ticks, as well as the skin. Dogs V3 and V4 also did not show any ticks. Dog REF yielded over the five days a total of 9 ticks which survived the observation time of 72 hours. Those ticks, after the 72 hours, were then taken out of the glasses and were placed onto the skin of a guinea pig (hair removed) where those ticks immediately tried to bite after having found a suitable place after reaching the area comprising hair. These ticks were removed using tweezers before they could bite and they were then immersed for 5 minutes into REF. After the immersion, those ticks were observed for 72 hours. After this additional observation time, ticks were put onto the guinea pig again. They tried to bite again.

The result shows that REF has a sufficient repellent aitivity with respect to ticks. However, no mortal activity can be obtained. The 43 ticks found on Dog K were immersed for 5 minutes into EX8 and as a result thereof, died within 30 minutes.

Results of Laboratory Tests Using Guinea Pigs

Two adult female guinea pigs obtained a treatment in order to remove the hair on an area of 4×4 cm. The skin and the surrounding hair were treated with approximately 2 ml EX8. After this treatment, one adult tick raised in the laboratory which had not been fed for two weeks was put onto the middle of the treated area using tweezers. Subsequently, the movement of the tick was observed. The guinea pigs were, contrary to other laboratory studies, not sedated in order to emulate a natural situation. During the test, the guinea pigs were fed with salad and they remained relatively calm since they were used to human. Immediately after the application of the ticks, it was evident that the ticks did not start, as usual, to wander around in order to look for a suitable place for biting (usually a place under the leg). Instead, the ticks, over a period of several minutes, did conduct a circular movement in the middle of the treated area. After those minutes, even a subtle movement of the guinea pigs led to the fact that the ticks fell off the guinea pigs, although ticks have the possibility to maintain their position even on smooth surface with their claws. The ticks which had fallen off the guinea pigs were placed into glasses and were observed for 72 hours. All ticks were dead after this observation.

Within the 8-hour test, 16 ticks in total were applied onto the two guinea pigs. None of those tick started to bite or to suck blood but all tick surprisingly died after contact with EX8.

The invention claimed is:

1. Composition comprising at least one hydrated compound of an unsaturated monoterpenoid together with at least one $C_6$-$C_{13}$ carboxylic acid, wherein the monoterpenoid is citronellal or an isomer thereof.

2. An insect repellent comprising the composition of claim 1 and at least one additive selected from solvents, dissolution accelerators, emulgators, dissolution enhancers, surface active agents, anti-foaming agents, salts, buffers, gel-forming agents, thickeners, film-forming agents, binders, lubricants, anti-sticking agents, flow regulating agents, moisturizers and drying agents, fillers, antioxidants, preservatives, odor correcting agents, colorants, or combinations thereof.

3. Composition according to claim 1, wherein the carboxylic acid is lauric acid.

4. An insect repellent comprising the composition of claim 3 and at least one additive selected from solvents, dissolution accelerators, emulgators, dissolution enhancers, surface active agents, anti-foaming agents, salts, buffers, gel-forming agents, thickeners, film-forming agents, binders, lubricants, anti-sticking agents, flow regulating agents, moisturizers and drying agents, fillers, antioxidants, preservatives, odor correcting agents, colorants, or combinations thereof.

5. A method to repel insects comprising applying the composition of claim 1 to an area to be protected.

* * * * *